(12) United States Patent
Kudo et al.

(10) Patent No.: US 7,976,524 B2
(45) Date of Patent: Jul. 12, 2011

(54) ABSORBENT ARTICLE

(75) Inventors: Jun Kudo, Kanonji (JP); Chiemi Habu, Kanonji (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 862 days.

(21) Appl. No.: 11/332,670

(22) Filed: Jan. 12, 2006

(65) Prior Publication Data

US 2006/0161123 A1 Jul. 20, 2006

(30) Foreign Application Priority Data

Jan. 20, 2005 (JP) ................. 2005-012380

(51) Int. Cl.
*A61F 13/15* (2006.01)
*A61F 13/20* (2006.01)

(52) U.S. Cl. ............................. 604/385.101
(58) Field of Classification Search ........... 604/385.101
See application file for complete search history.

(56) References Cited

U.S. PATENT DOCUMENTS

| 3,929,135 | A | * | 12/1975 | Thompson | 604/385.08 |
| 4,323,069 | A | | 4/1982 | Ahr et al. | |
| 5,783,014 | A | * | 7/1998 | Biagioli et al. | 156/209 |
| 2002/0107495 | A1 | * | 8/2002 | Chen et al. | 604/365 |
| 2004/0116882 | A1 | * | 6/2004 | Erspamer et al. | 604/359 |

FOREIGN PATENT DOCUMENTS

| JP | S57-089861 | | 6/1982 |
| JP | S64-062158 | | 3/1989 |
| JP | H06-000425 | U | 1/1994 |
| JP | 07-328061 | A | 12/1995 |
| JP | 08-164159 | A | 6/1996 |
| JP | H09-187476 | | 7/1997 |
| JP | 10-500048 | A | 1/1998 |
| JP | H11-509458 | | 8/1999 |
| JP | 2000-342624 | A | 12/2000 |
| JP | 2001-061891 | A | 3/2001 |
| JP | 2001-187087 | A | 7/2001 |
| JP | 2001-277401 | A | 10/2001 |
| JP | 2003-102772 | A | 4/2003 |
| JP | 2004-208833 | A | 7/2004 |
| WO | WO-95/31166 | A1 | 11/1995 |
| WO | WO 9531166 | A1 * | 11/1995 |
| WO | 9741818 | A1 | 11/1997 |

OTHER PUBLICATIONS

Notice of Reasons for Rejection mailed Jul. 21, 2009 in corresponding Japanese Patent Application No. 2005-012380.

* cited by examiner

*Primary Examiner* — Melanie J Hand
(74) *Attorney, Agent, or Firm* — Morrison & Foerster LLP (57) ABSTRACT

An absorbent article, in which an erroneous impression of replacement time is not given to a wearer, includes an absorbent body, a front sheet covering the absorbent body, and a rear sheet, a pair of masking members being disposed along a longitudinal direction of the absorbent body, close to two ends of a short direction of the absorbent body, the masking members being of porous film having pores continuous in the direction of thickness, the thickness thereof preferably being 0.4 mm or greater under a load of 20 g/cm$^2$. By this means, seepage of fluid at the side margins of the front sheet is deferred and misunderstanding of replacement time by the wearer is prevented.

10 Claims, 5 Drawing Sheets

ABSORBENT ARTICLE

This application is based on and claims the benefit of priority from Japanese Patent Application No. 2005-012380, filed on Jan. 20, 2005, the content of which is incorporated herein by reference.

BACKGROUND OF THE INVENTION

1. Field of the Invention

The present invention relates to absorbent articles, such as sanitary napkins and the like, that have a concealing effect for concealing body fluids such as menstrual blood and the like, during use.

2. Related Art

Absorbent articles for absorbing body fluids such as menstrual blood and the like are generally formed of a front sheet that contacts the body and is easy for fluids to penetrate, a rear sheet, being a face opposed thereto, that is difficult for fluids to penetrate, and an absorbent body interposed between the two sheets. Moreover, the absorbent articles normally have a longitudinal direction lying in the front-back direction of a wearer when worn, and a short direction (lateral direction) lying in the left-right direction of the wearer. In these kinds of absorbent articles, in recent years the absorbency of the absorbent body is improving in order to eliminate underwear staining and the like.

When the absorbent body absorbs the body fluids, the body fluids are uniformly diffused to the front, rear, left, and right of the absorbent body by capillary action. At this time, in the above-described absorbent articles, the diffusion distance in the short direction is shorter than in the longitudinal direction. As a result, the body fluids firstly diffuse to both ends of the short direction of the absorbent body. After that, they diffuse to both ends of the longitudinal direction, at which stage the absorptive capacity of the absorbent body is reached.

However, at the stage of diffusion to both ends of the short direction, diffused body fluids migrate by body pressure to the front sheet, and in cases where the wearer visually perceives this migration, the wearer mistakenly thinks that at this stage the capacity of the absorbent body is reached. As a result, there is a problem in that article replacement is carried out without the complete absorptive capacity being reached.

In order to solve these types of problems, in Japanese Patent Application Laid Open No. Hei10-500048(hereinafter Patent Document 1), a masking member is arranged at a peripheral region of the absorbent body. In this way, a concealing effect is produced in the vicinity of the absorbent body, and it is possible to prevent giving an impression to the wearer that the absorbent body is in a saturated state (i.e., that it is time for replacement.)

SUMMARY OF THE INVENTION

In an absorbent article disclosed in Patent Document 1, by disposing a masking member in the peripheral area, a visual impression that it is replacement time is not mistakenly given to the wearer. However, since the masking member is disposed all around the product, a masking effect is also realized at both ends of the longitudinal direction of the product, so that, conversely, there are cases where the wearer does not visually understand a proper replacement time.

Furthermore, the absorbent article is used in a state in which body pressure is acting; however, when body pressure acts, body fluid previously captured by the absorbent body has a tendency to move back (wet back) to the front sheet. Thus, if the masking member does not also have a capability to temporarily prevent passage of the body fluid, the body fluid that diffuses from the absorbent body to the outside permeates the masking member and adheres to and soils the front sheet, as a result of which the masking effect cannot be adequately realized. However, with regard to this type of capability to prevent passage of the body fluid, there is no discussion of the masking member in Patent Document 1.

The present invention takes into account the above types of problems and has as an object the provision of an absorbent article in which a mistaken impression that it is replacement time is not given to the wearer.

More specifically, the present invention provides the following type of absorbent article.

In a first aspect of the present invention, an absorbent article includes a front sheet, a rear sheet, and an absorbent body disposed between the two sheets, the absorbent article having, when worn, a longitudinal direction lying in the front-back direction of the wearer, and a short direction lying in the left-right direction of the wearer, in which a pair of masking members is disposed in the vicinity of the two ends of the short direction of the absorbent body, along the longitudinal direction.

According to a first aspect of the present invention, by disposing the masking members as a pair along the longitudinal direction, in the vicinity of the two ends of the short direction of the absorbent body, even if the body fluid, captured by the absorbent body and diffused by capillary action from there to outside of the absorbent body, moves back to the front sheet by body pressure, it is possible to conceal the front sheet portion by the masking members.

However, the masking members are not disposed in the vicinity of the two ends of the longitudinal direction of the absorbent body. As a result, since a concealing effect is not realized in the vicinity of the two ends of the longitudinal direction, the wearer can visually determine the final replacement time. Furthermore, since the masking members are of a material harder than the absorbent body and relatively resistant to body pressure, when disposed at the position of the excretion opening which has a mucous nature, a sense of discomfort is given to the wearer; in the present invention, however, since the masking members are not disposed close to the two ends of the longitudinal direction of the absorbent body, a feeling of discomfort is not given.

In this way, according to the present invention, by disposing the masking members as a pair along the longitudinal direction only, the visual effect when fluid is absorbed is different to that of the portion where a masking member is not disposed, and it is possible to make the wearer aware of the correct replacement time. In addition, the "masking members" in the present invention have a prescribed bulk that can block off the fluid. Specifically, porous film, non-woven fabric, urethane foam or the like are used.

A second aspect of the absorbent article as described in the first aspect of the present invention, the masking members are of porous film having pores that are continuous in the direction of thickness.

According to the second aspect of the present invention, by the masking members being of porous film with pores that are continuous in the direction of thickness, it is possible to capture the body fluid discharged by body pressure and to temporarily retain it within the pores. In this way, it is possible to prevent diffusion by capillary action from both ends of the short direction of the absorbent body from progressing to leakage.

A third aspect of the absorbent article as described in the second aspect of the present invention, the thickness of the porous film is 0.4 mm or greater under a load of 20 g/cm$^2$.

According to a third aspect of the present invention, by making the thickness of the porous film in the abovementioned range, contact between the absorbent body and the front sheet can be prevented even in a state where body pressure is acting, it becomes possible to prevent adherence of the fluid that seeps out to the front sheet, and a concealing effect can be realized. The thickness of the porous film may be 0.4 mm or greater under a load of 20 $g/cm^2$, but preferably 0.55 mm or greater, and even more preferably 0.7 mm or greater. This is because even if the body fluid does not seep to the front sheet, since on seeing the red color of menstrual blood, the visual effect of the front sheet may cause concern to the wearer, it is preferable to have as large a distance as possible from the absorbent body that absorbs the body fluid.

A forth aspect of the absorbent article as described in the second or the third aspects of the present invention, the porous film is an open pore film, on one face of the open pore film, circumferential ribs are formed, extending from the edges of each of the pores on the other face, and the open pore film is disposed so that the one face is facing the absorbent body side.

According to a fourth aspect of the present invention, by arranging the circumferential ribs extending from the edges of the pores, on the one face of the open pore film, the bulk (thickness) of the open pore film can be increased, and in addition, "recesses" created by adjacent ribs are formed on the "one face." By disposing this one face so that it faces the absorbent body, the body fluid discharged by body pressure can be captured by the "recesses," and even in a state where body pressure is acting, body fluids can be more precisely prevented from seeping to the front sheet.

A "rib" in the present invention is a part which is extending from an opening of the pore. Therefore, the open pore film has a three dimensional structure. The rib acts as a valve in the open pore film to adjust a flow of a body fluid when it moves back to the front sheet from the absorbent body. A "circumferential" in the present invention is a state when the rib extends around the opening of the pore circumferentially.

In a fifth aspect of the absorbent article as described in fourth aspect of the present invention, the circumferential ribs have a tapered shape with reduced diameter towards the extremity thereof.

According to fifth aspect of the present invention, by the circumferential ribs having a tapered shape with reduced diameter towards the extremity thereof, the volume of the "recesses" can be increased, and inlets to pores can be narrowed. In this way, since the body fluid that can be captured by the "recesses" can be increased, and conversely the body fluid volume passing through the pores can be decreased, the body fluid can be temporarily retained within the "recesses," and even in a state where body pressure is acting, can be more precisely prevented from passing through the pores and seeping to the front sheet. In addition, with this type of disposition, the ability to conceal body fluids can be further increased.

In sixth aspect of the absorbent article as described in the fourth or the fifth aspects of the present invention, the open pore film is disposed as a plurality of stacked layers, and at least the open pore film disposed on the absorbent body side is disposed so that the one face is facing the absorbent body.

According to sixth aspect of the present invention, by using the plurality of layers of the open pore film, the distance from the absorbent body to the front sheet becomes longer, so that even in cases where body pressure is acting, the body fluid can be more effectively prevented from seeping to the front sheet. Furthermore, since the concealing effect with regard to the visual appearance from the front sheet is increased, the red color of menstrual blood and the like is not seen, and it can be made more difficult for the wearer to be given an unpleasant feeling.

In seventh aspect of the absorbent article as described in the second or third aspects of the present invention, the porous film is a foam film having continuous cells.

According to seventh aspect of the invention, the porous film having pores continuous in the direction of thickness can be easily obtained. Furthermore, by adjusting the extent of the foam, the size and number of the pores can be made adjustable.

In the absorbent article described in any of the first through seventh aspects of the present invention, the masking members are disposed between the front sheet and the absorbent body.

According to eighth aspect of the present invention, even if the body fluid, captured by the absorbent body and diffused from there by capillary action to the outside of the absorbent body, moves back to the front sheet by body pressure, the front sheet portion can be concealed by the masking members. That is, firstly, the body fluid flows in from approximately the center portion of the front sheet, is temporarily captured by the absorbent body, and is partially retained. The absorbed body fluid is diffused by capillary action in an approximately concentric fashion to the front, rear, left and right of the absorbent article. The diffused body fluid is temporarily captured in the various diffused areas of the absorbent body, and is partially retained. The body fluid other than this retained fluid portion generally seeps by the action of body pressure to the front sheet. However, since the masking members are disposed close to the two ends of the short direction of the absorbent body, they come between the front sheet and the absorbent body, and by this means the body fluid can be prevented from passing through the masking members and moving back to the front sheet.

In the absorbent article described in any of the first through seventh aspects of the present invention, the masking members are disposed above the front sheet.

According to ninth aspect of the present invention, even in cases where the body fluid diffused from close to both ends of the short direction of the absorbent body moves back to the front sheet, the front sheet portion can be concealed by the masking members thereon.

In the absorbent article described in any of the first through ninth aspects of the present invention, the masking members, the front sheet, the rear sheet and the absorbent body are integrally joined in the vicinity of the two ends of the short direction of the absorbent body.

According to tenth aspect of the present invention, as described above, the body fluid flows in from the front sheet where the masking members are not disposed, and is diffused in the absorbent body; however, since the density of the joining portion is higher than other locations, the body fluid runs easily. For example, in cases where the front sheet is formed of non-woven fabric, the body fluid stored in the absorbent body by capillary action of the front sheet fabric is soaked up, and from the front sheet, seepage appears to occur at the joining portion. However, by including the masking members in the joining, the body fluid does not appear to seep out at the joining portion, and the sense of safety is increased regarding side leakage.

In particular, in cases where porous film is used for the masking members, since by the joining, pores of the joint portion collapse and become like a flat film, contact between the front sheet and the absorbent body can be prevented more effectively. In addition, the joining method is not particularly limited, and a hot-melt adhesive joint or the like, or heat sealing may be used.

In the eleventh aspect of the present invention, the absorbent article described in any of first through tenth aspects of the present invention, the masking members may be pigmented.

According to eleventh aspect of the present invention, for example, by pigmenting the masking members with a similar type of color to that of the body fluid, it is possible to further increase the concealing effect. More specifically, by giving a Hunter value of below 60 on the Hunter Lab Color-difference Meter to the masking members, the concealing effect can be further increased.

In the twelfth aspect of the present invention, the absorbent article described in any of the first through tenth aspects of the present invention, the masking members are disposed in a state with tensioning applied in the longitudinal direction.

According to the twelfth aspect of the present invention, by applying tension in the longitudinal direction, the product flexes easily in the front side and fits the shape of the body more easily, and the wearability feeling can be improved. In such cases, it is preferable that a tensioning force is applied from 1.03 to 1.45 times the longitudinal direction.

According to the absorbent article related to the present invention, by disposing the masking members at the two sides of the absorbent body, seepage of fluid at the side margins of the front sheet is eliminated, and an erroneous visual impression that it is replacement time is not given to the wearer. Furthermore, since the area of skin that is soiled is limited, the feeling of discomfort given to the wearer is reduced.

DETAILED DESCRIPTION OF THE INVENTION

A preferable embodiment of the present invention will be explained below, referring to the drawings, with a sanitary napkin as an example of an absorbent article. Furthermore, identical constituent elements are given the same numerals, and duplicate explanations thereof are omitted or simplified. In addition, in the present invention, percentage expressions indicate percentages by weight.

Overall Configuration

Figure 1:
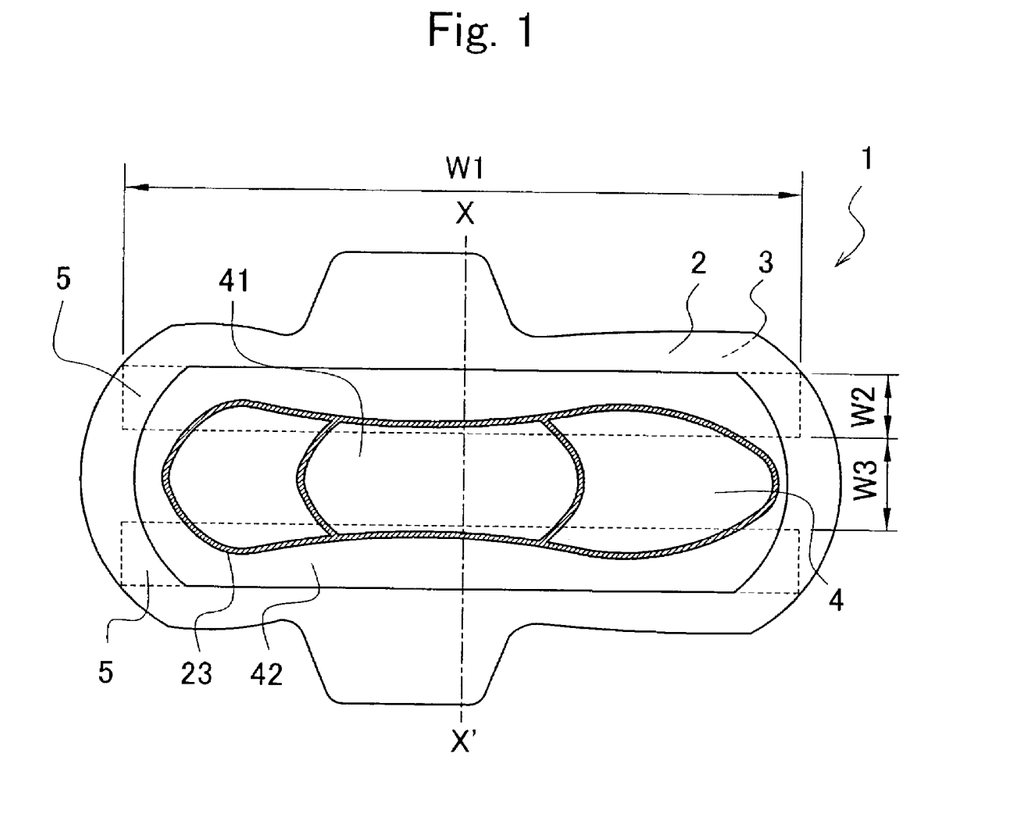
FIG. 1 shows a sanitary napkin related to an embodiment.
Figure 2:
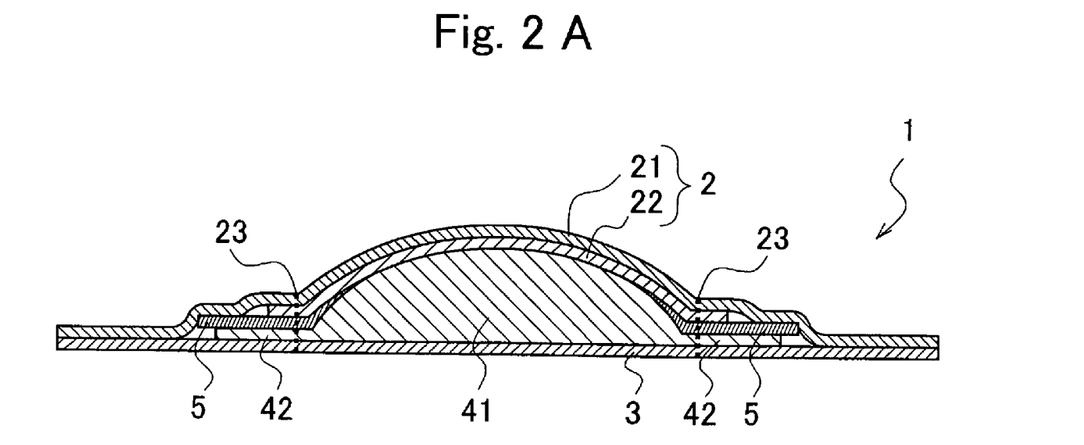
FIG. 2A shows a cross-section X-X' of the sanitary napkin related to the embodiment.
FIG. 2B shows a cross-section of a sanitary napkin related to another embodiment.

FIG. 1 is a plane view showing a sanitary napkin in one embodiment of the present invention, and FIG. 2A is a cross-sectional view X-X' of FIG. 1. As shown in FIG. 1 and FIG. 2A, the sanitary napkin 1 mainly includes a front sheet 2, a rear sheet 3, an absorbent body 4 interposed between the two sheets, and a pair of masking members 5 disposed between the front sheet 2 and the rear sheet 3, being close to the two ends of the short direction of the absorbent body 4. Furthermore, in this embodiment the short direction is the direction X-X' in FIG. 1 and the longitudinal direction is the direction of W1 in FIG. 1.

The front sheet 2 is formed of a top sheet 21 that is easily permeable by fluids, and a second sheet 22 that is easily permeable by fluids or has fluid retainability, and that forms a cushion layer. The rear sheet 3 is difficult for fluids to permeate. The absorbent body 4 is formed of an absorbent body core 41 that has fluid retainability, and an extended portion 42 that extends from the lower area thereof; the absorbent body core 41 is disposed so as to lie between the front sheet 2 and the rear sheet 3, and the extended portion 42 is disposed so as to form a layered buildup between the front sheet 2 and the rear sheet 3.

A pair of masking members 5 in the form of strips is arranged along the longitudinal direction on the extended portion 42, close to both ends of the short direction of the absorbent body 4. The top sheet 21 and the second sheet 22, being the front sheet 2, the absorbent body 4, and the rear sheet 3 are each joined by bonding using hot-melt adhesive (hereinafter referred to as HMA). Furthermore, on the lower side of the rear sheet 3, a non-slip member (not shown in the figure) is arranged at a position corresponding to the bottom of the absorbent body 41 and the masking members 5.

Furthermore, as shown in FIG. 1, the front sheet 2, the extended portion 42 and the rear sheet 3 are fixed by a heat-sealed portion 23 of circumferential shape, and a part of the heat-sealed portion 23 acts on the masking members 5, close to both ends of the short direction of the absorbent body 4. Thus, as shown in FIG. 2A, at the positions where the masking members 5 exist, the front sheet 2, the masking members 5, the extended portion 42, and the rear sheet 3 are fixed by the heat-sealed portion 23.

Furthermore, as shown in FIG. 2B, the masking members 5 of the present invention may be configured to be disposed on top of the front sheet.

Masking Members

In FIG. 1, a length W1 in the longitudinal direction of the area in which the masking members 5 are arranged is most preferably equivalent to that of the sanitary napkin 1 related to the present embodiment, a length of 40 mm or greater being preferable, and 50 mm or greater being more preferable. In addition, since the visual effects vary according to product length, the length must be 20% of the product length or greater. Furthermore, a length W2 in the short direction is preferably approximately the same or greater than the length from the end edge of W3 to the end edge of the absorbent body 4. In addition, the distance between the masking members, W3, is preferably between 20 mm and 70 mm, and is more preferably between 26 mm and 50 mm. If W3 is 20 mm or less, there is a possibility that body fluids discharged from the excretion opening position will seep into the absorbent body core 41 from the top sheet 21 and the second sheet 22 that are arranged above the masking members 5, and the masking effect will not be realized. Furthermore, if W3 is 70 mm or greater, since a user confirms a state in which body fluid is diffused, visual effects of the masking are not exhibited.

Woven material or non-woven material, open pore film, or porous foam such as urethane foam or the like are used for the masking members 5. Synthetic fabric (for example, polymer fabric such as polyester fabric, polypropylene fabric, or polyethylene fabric) and the like may be used for the woven material or non-woven material. Among these, as described below, open pore film is permeable to body fluids; however, it is more preferable to use a film in which the tendency to pass fluid in a reverse direction towards the skin of the wearer is small. Furthermore, if mainly hygroscopic fabric is blended in the masking members, since there is a possibility that the masking members may absorb the body fluid and the body fluid may migrate to the front sheet, it is not preferable to use materials mainly including natural fabric.

In the above description, a porous film with pores continuous in the direction of thickness is preferable for the masking members 5 related to the present invention, and more preferably, the porous film is an open pore film, circumferential ribs being formed on one face of the open pore film, extending from the edges of each of the pores of the other face, the circumferential ribs having a tapered shape with reduced diameter towards the extremity thereof.

Figure 3:
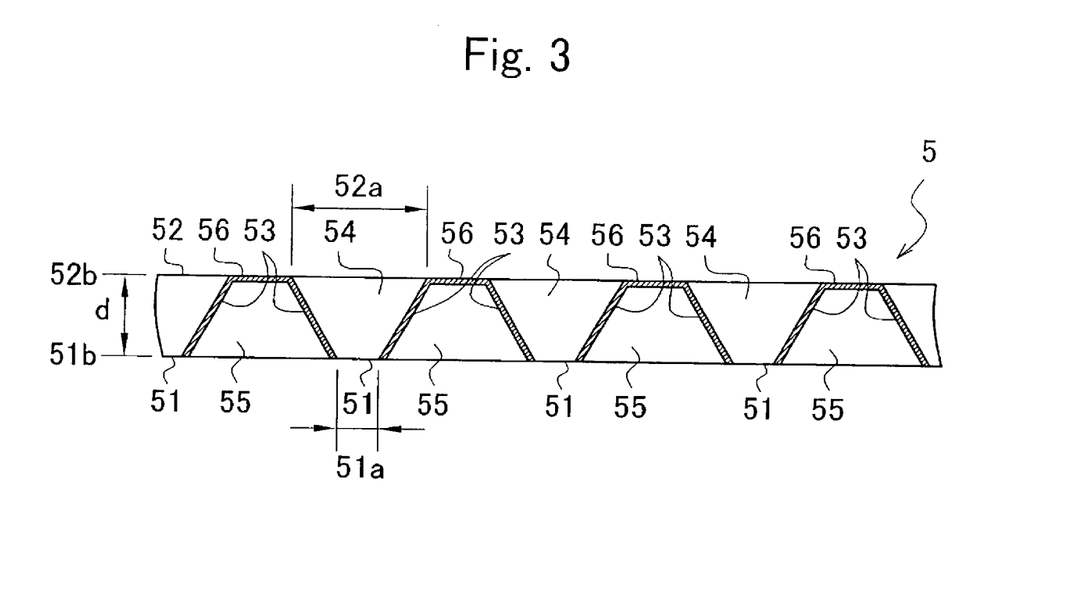
FIG. 3 shows an enlarged cross-section of a preferable masking member.

Specifically, a structure of a type shown in FIG. 3 is preferable. FIG. 3 is an enlarged cross-sectional view of a preferable masking member.

This masking member 5 is an open pore film, with the hatched area in the figure indicating film base material 56. Portions other than the film base material 56 are open spaces, formed by alternating pores 54 (open pore portion) and recesses 55. That is, in this open pore film, from a planar film that has a base line 52b in the figure as base, circumferential walls of the pore 54 portions, that form the open pores, extend to a base line 51b, so as to have a tapered shape with reduced diameter towards the extremity thereof, and in the present invention constitute ribs 53. By means of these ribs 53, a low open pore ratio face 51 having a small open pore area 51a whose surface open pore diameter is small (the bottom of FIG. 3, at the same position as the base line 51b), and a high open pore ratio face 52 having a large open pore area 52a whose surface open pore diameter is large (the top of FIG. 3, at the same position as the base line 52b), are formed as the two faces of the open pore film.

The ribs 53 are preferably formed so that the thickness d of the open pore film in FIG. 3 is 0.4 mm or greater under a weighting of 20 $g/cm^2$. Furthermore, the open pore diameter in the small open pore area 51a is preferably greater than or equal to 0.2 mm and less than or equal to 0.8 mm, and the open pore diameter in the large open pore area 52a is preferably greater than or equal to 0.6 mm and less than or equal to 1.3 mm. (Note that the small open pore area is smaller than the large open pore area.) The open pore ratio (area ratio) of the pores 54, in the small open pore area, is preferably greater than or equal to 5% and less than or equal to 45%. This type of open pore film can be obtained using conventionally known manufacturing methods.

In a case in which the masking member is an open pore film formed to have a three dimensional structure in the open pore film, the rib which is extending from the opening of the pore is crumpled at the heart-sealed portion, and it can block the front sheet from contacting the absorbent body.

Figure 4:
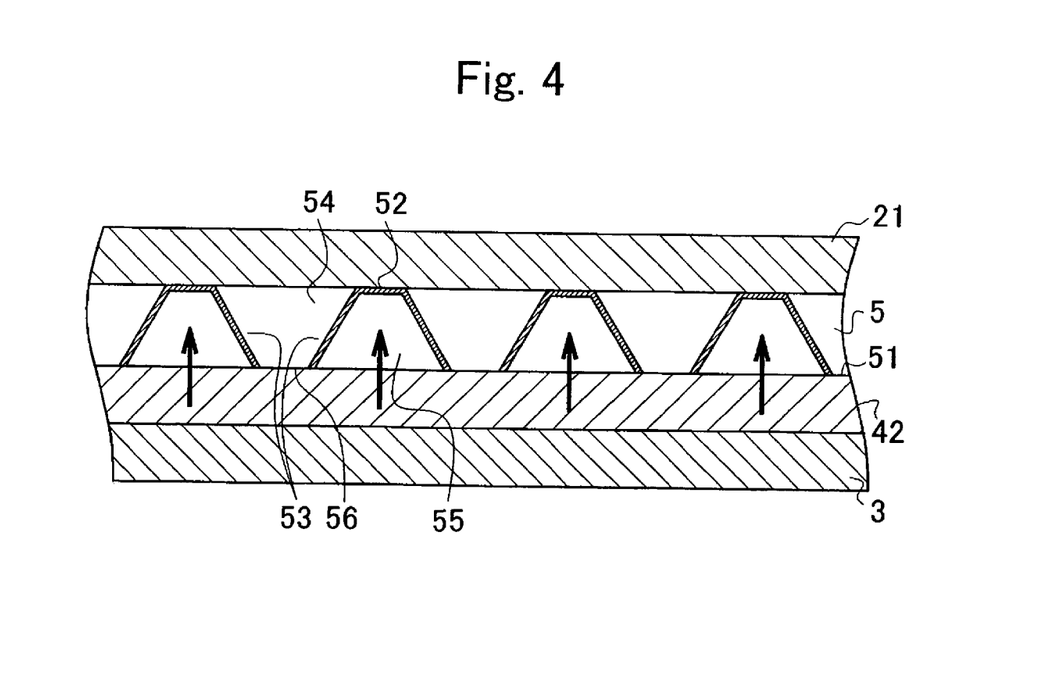
FIG. 4 shows an enlarged cross-section of the vicinity of a masking member in FIG. 1.

In this embodiment, as shown in FIG. 4, the low open pore ratio face 51 is disposed so as to be touching the extended portion 42 of the absorbent body 4. This low open pore ratio face 51 corresponds to "one face" in the present invention, and the high open pore ratio face 52 corresponds to "the other face" in the present invention. By using this type of layout, in a state where body pressure is acting, even in cases where body fluid "wet back" occurs in the direction of the arrows in the figure, it is possible to temporarily retain the body fluid within the recesses 55, and to more accurately prevent the body fluid from passing through the pores and seeping to the front sheet side.

Figure 5:
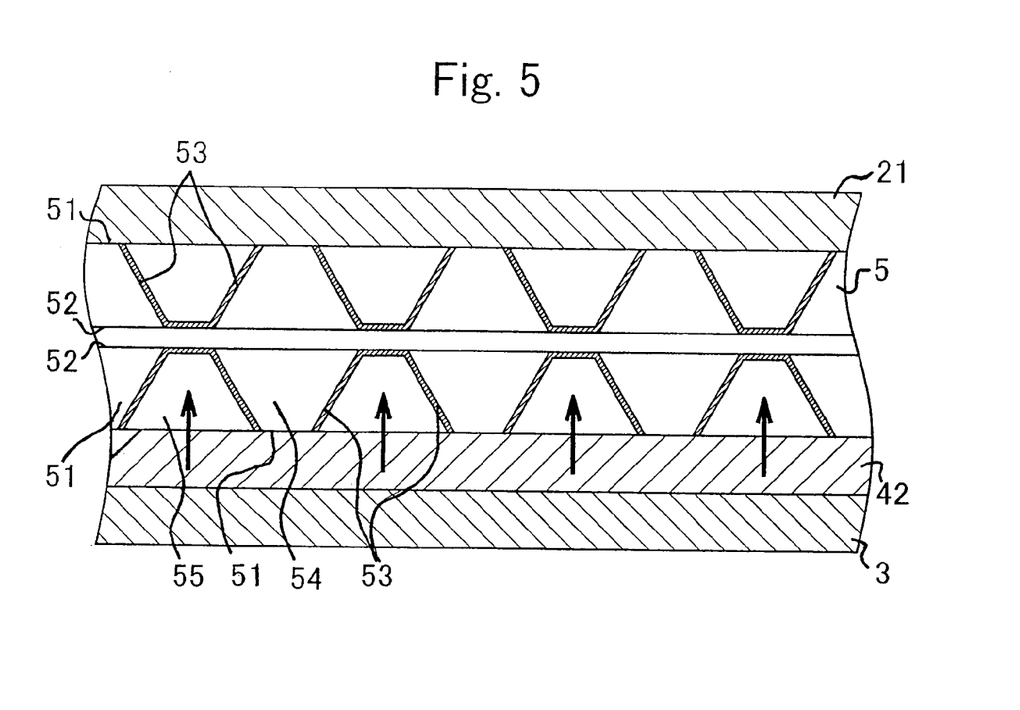
FIG. 5 shows a stacked pattern of a masking member related to the present invention.
Figure 6:
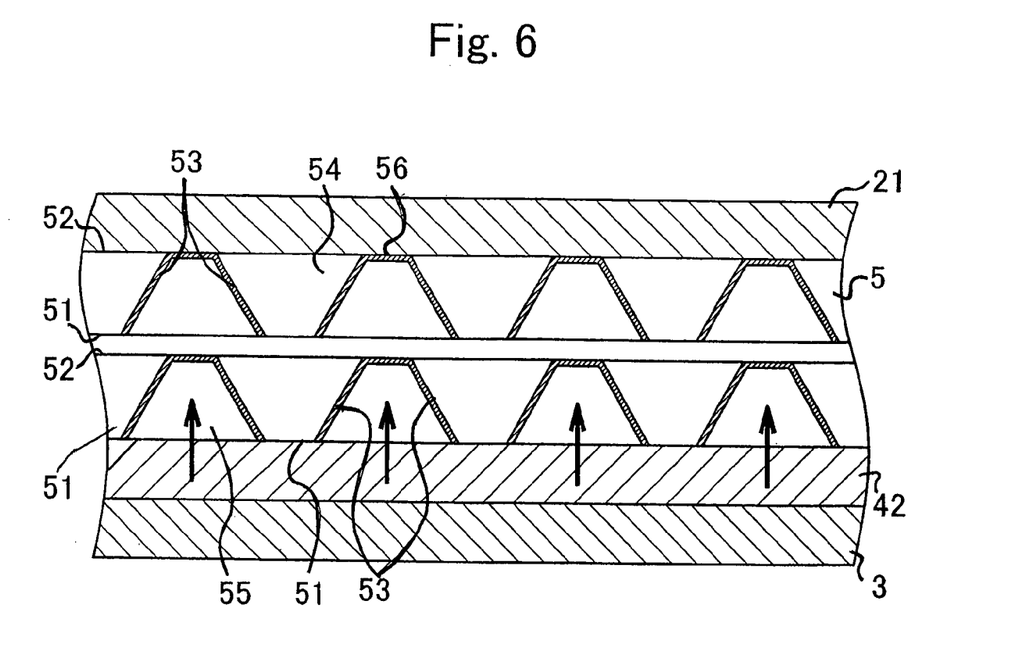
FIG. 6 shows a stacked pattern of a masking member related to the present invention.
Figure 7:
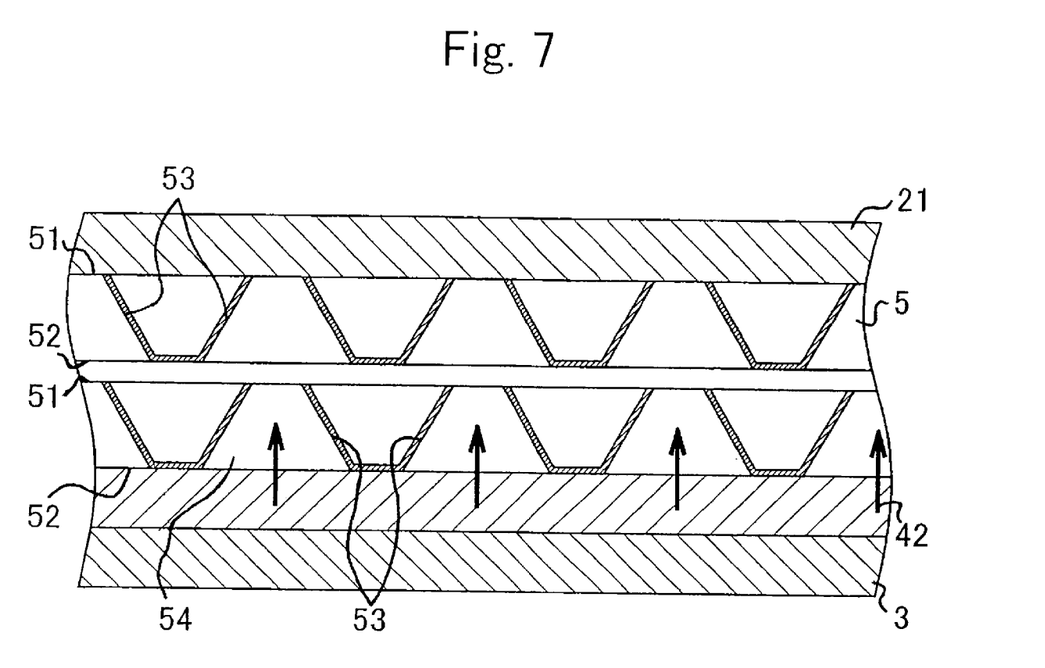
FIG. 7 shows a stacked pattern of a masking member related to the present invention.

Furthermore, this porous film may be disposed as a single layer only or may be disposed as a plurality of stacked layers; at least, however, the low open pore ratio face 51 is preferably disposed so as to touch the extended portion 42 of the absorbent body 4. FIGS. 5 and 6 show one example of a preferable stacking method for cases where two layers are stacked; and FIG. 7 shows a non-preferable stacking method for cases where two layers are stacked. Furthermore, this stacking method is explained in more detail in an embodiment described below.

Component Members

Next, members of which the sanitary napkin 1 is composed are explained.

The top sheet 21 that forms the front sheet is hydrophilic and is of a material that does not irritate the skin. Regarding such materials, point bond, spun lace, and spun bond non-woven fabrics and the like may be cited. An open pore film may also be used. Among these, low-density, through-air non-woven fabric with good surface texture is most preferable. Furthermore, the through-air non-woven fabric may, for example, with a coating of 35 $g/m^2$, be a cotton mix of 0.6 mm thickness with proportions of: 50% of 2.6 dtex, 51 mm fiber with core-in-sheath composite thermoplastic fiber of polyethylene terephthalate (including 1.1% titanium oxide)-polyethylene, coated with hydrophilic oil solution, 30% of 2.2 dtex, 44 mm fiber with core-in-sheath composite thermoplastic fiber of polyethylene terephthalate (including 1.1% titanium oxide)-polyethylene, coated with hydrophilic oil solution, and 20% of 2.2 dtex, 44 mm fiber with core-in-sheath composite thermoplastic fiber of polyethylene terephthalate (including 1.1% titanium oxide)-polyethylene, coated with water-repelling oil solution. In addition, since titanium oxide is added to the core of the core-in-sheath structure, compared to situations where titanium oxide is not added, the surface has good slip and drape properties, and the texture is good. Since through-air non-woven fabric is used, compared to other non-woven fabrics (spun bond, spun lace and the like), a preferable configuration can be realized, possessing bulk and with many voids provided.

Furthermore, a coating of 15-100 $g/m^2$ is preferable, and 30-60 $g/m^2$ is more preferable. Having a bulk of 0.4 to 2.0 mm, and additionally with 1.0% or greater titanium oxide included in the core of the core-and-sheath structure of the non-woven fabric, there is not much settling of the front sheet during usage, distance from the absorbent body is gained, and in addition, the front sheet itself can also increase concealment. Furthermore, by including up to 30% water repelling fiber, the effect of curtailing diffusion in the front sheet is obtained; and by blending the water repelling fiber, the effect of curtailing absorption of fluid from the absorbent body is obtained. If the coating is 15 $g/m^2$ or less, sufficient surface strength cannot be obtained and there is a danger that breakage may occur during usage. Moreover in cases of 100 $g/m^2$ or greater, excessive roughness may occur, and a feeling of discomfort during usage may occur. Furthermore, with a density of 0.12 $g/cm^3$ or less, particular limitation is not required as long as the fiber has fluid permeability. For cases where the density is greater than this, it is difficult to smoothly permeate between the fibers of the front sheet. For cases of menstrual blood, viscosity is high in comparison to urine and the like, so it is preferable to have as low a density as possible.

For the second sheet 22, that the front sheet includes, a material having fluid permeability or fluid retainability is used. For such a material, as for the top sheet 21, point bond, spun lace, and spun bond non-woven fabrics and the like may be cited; however, a through-air non-woven fabric of low density and good surface texture is most preferable. Compared to other non-woven fabrics (spun bond, spun lace and the like), this through-air non-woven fabric is preferable because it possesses bulk and many voids can be provided. Specifically, regarding the through-air non-woven fabric used for the second sheet 22, for a coating of 20 g/m², a cotton mix of core-in-sheath composite thermoplastic fiber of polypropylene-polyethylene, with 3.3 dtex, 45 mm and 2.2 dtex, 45 mm in a ratio of 70:30 by weight may be cited.

Besides the through-air non-woven fabrics, air laid pulp with fluid retainability may also be used. Since this air laid pulp possesses hydrophilic effects in comparison to the through-air non-woven fabric, it is excellent in that it draws menstrual blood retained in the front sheet. Furthermore, this air laid pulp is configured to hold a frame using chemical fiber, and is not easily affected by fluid; however, the through-air non-woven fabric in which most of the structure is formed of chemical fiber is more preferable.

Furthermore, the density of the second sheet 22 is preferably in the range 0.1 to 0.01 g/cm³. Where this value is greater than 0.1 g/cm³, voids are few and diffusion of menstrual blood is bad. In addition, where it is lower than 0.01 g/cm³, a large number of voids are obtained, but since the frame for supporting the voids can become weak, this is not preferable. Further, the second sheet 22 can, for example, be bonded to the rear side of the top sheet 21 by a coating of HMA in a spiral shape.

Since the absorbent body 4 has a capability for absorbing and retaining menstrual blood, absorptive sheets such as air laid pulp, non-woven fabrics including absorptive fabrics (spun lace, through-air methods and the like) and the like are used. As one example that may be cited, for a pulp coating of 200 g/m², and a polymer coating of 4 g/m² (the polymer is distributed over the whole body), a mixture of absorptive polymer and chemical pulp, with the pulp and the polymer evenly distributed over the whole body, is wrapped in 15 g/m² tissue.

Furthermore, for a back sheet that forms the rear sheet 3, a fluid-impermeable film consisting mainly of polyethylene (PE), polypropylene (PP), and the like, an air-permeable film, a composite sheet with a fluid-impermeable film laminated on one side of a spun bond or similar non-woven fabric, or the like, may be cited. Specifically, in consideration of suppleness that does not damage wearability, the fluid-impermeable film is formed mainly of low density polyethylene (LDPE) in which the density is in the range 0.900 to 0.925 g/cm³, with a coating of 15 to 40 g/m².

EMBODIMENT EXAMPLE

For a sanitary napkin related to the present embodiment, the following illustrates the results of examining the masking effects of the masking members thereof, using various types of open pore film.

Porous Film A

For the masking members, after manufacturing a membrane by making a combination of proportions: 68% low density polyethylene (MFR 15 g/10 min, 0.915 g/cc density), 28% low density polyethylene (MFR 7 g/10 min, 0.917 g/cc density), 3.8% titanium oxide, and 0.2% hydrophilic agent (glycerin fatty acid ester, as one example), open pores are formed by a well known method, and an open pore film is created as shown in FIG. 3 (25 g/m² coating, 25% open pore ratio, 0.61 mm open pore diameter for the small open pore area 51a, and 0.94 mm open pore diameter for the large open pore area 52a.)

Porous Film B

For the masking members, a film is manufactured by making a combination of proportions: 57.6% high density polyethylene (MFR 30 g/10 min, 0.950 g/cc density), 38.4% low density polyethylene (MFR 7 g/10 min, 0.917 g/cc density), 3.8% titanium oxide with plurality of pores, and 0.2% hydrophilic agent, open pores are formed using a well known method, and an open pore film is created as shown in FIG. 3 (20 g/m² coating, 25% open pore ratio, 0.55 mm open pore diameter for the small open pore area 51a, and 0.82 mm open pore diameter for the large open pore area 52a.)

Porous Film C

For the masking members, after manufacturing a membrane by making a combination of proportions: 57.6% high density polyethylene (MFR 30 g/10 min, 0.950 g/cc density), 38.4% low density polyethylene (MFR 7 g/10 min, 0.917 g/cc density), 3.8% titanium oxide with plurality of pores, and 0.2% hydrophilic agent, open pores are formed using a well known method, and an open pore film is created as shown in FIG. 3 (25 g/m² coating, 25% open pore ratio, 0.53 mm open pore diameter for the small open pore area 51a, and 0.81 mm open pore diameter for the large open pore area 52a.)

Urethane Foam

For the masking members, polyester-type polyurethane foam of 1.8 mm thickness, 28 kg/cm³ density, and 45 to 50 cells (continuous cell type) per inch are used (product name: WG-(B), manufactured by Bridgestone Chemical Products Co. Ltd.)

Furthermore, for the front sheet, with a through-air non-woven fabric coating of 35 g/m², a cotton mix of thickness 0.6 mm may be used, having proportions: 50% of 2.6 dtex, 51 mm fiber with core-in-sheath composite thermoplastic fiber of polyethylene terephthalate (including 1.1% titanium oxide)-polyethylene, coated with hydrophilic oil solution, 30% of 2.2 dtex, 44 mm fiber with core-in-sheath composite thermoplastic fiber of polyethylene terephthalate (including 1.1% titanium oxide)-polyethylene, coated with hydrophilic oil solution, and 20% of 2.2 dtex, 44 mm fiber with core-in-sheath composite thermoplastic fiber of polyethylene terephthalate (including 1.1% titanium oxide)-polyethylene, coated with water-repelling oil solution. In addition, for the second sheet, a cotton mix, 0.3 mm thick, is used, of core-in-sheath composite thermoplastic fiber of polypropylene-polyethylene, with 3.3 dtex, 45 mm, and 2.2 dtex, 45 mm, in a ratio of 70:30 by weight. Furthermore, for the absorbent body, a 150 g/m² coating of ground pulp sandwiched by 15 g/m² tissue is used, the ground pulp density being 0.054 cm/m³.

Seepage Test

A 10 cm square cut was taken for each test sample, a 10 ml drop of artificial blood was put on the absorbent body, one minute after adding the drop two second sheets and a front sheet were additionally piled on each test sample, and a 2 kg spindle with a 10 cm square base was placed thereon. Three minutes after applying pressure the weight was removed, and a determination was made as to whether the artificial blood had adhered to the front sheet. Furthermore, the thickness of the masking member was measured using a thickness gauge (thickness gauge model UF-60, manufactured by Daiei Kagaku Seiki Manufacturing Co. Ltd.) In addition, open pore diameters in the small open pore area and the large open pore area were measured based on an enlarged photograph taken with an electron microscope, and were expressed as the average value of longitudinal and lateral dimensions.

TABLE 1

| Material | Number of layers | Masking member disposition, stacked pattern | In mm under pressure 3.3 g/cm² | In mm under pressure 20 g/cm² | Seepage test results |
|---|---|---|---|---|---|
| Porous film A | 1 | low-high | 0.45 | 0.36 | S |
| Porous film A | 2 | low-high-high-low | 0.93 | 0.75 | NSAM |
| Porous film B | 1 | low-high | 0.48 | 0.37 | S |

TABLE 1-continued

| Material | Number of layers | Masking member disposition, stacked pattern | In mm under pressure 3.3 g/cm² | In mm under pressure 20 g/cm² | Seepage test results |
|---|---|---|---|---|---|
| Porous film B | 2 | low-high-low-high | 0.99 | 0.81 | NSAM |
| Porous film C | 1 | low-high | 0.49 | 0.43 | NS |
| Urethane | 1 | | 1.76 | 1.71 | NSAM |

Explanation of Terms (Structure of Stacked Pattern)
"low-high": the structure disposed in order: absorbent body, low open pore ratio face, high open pore ratio face (corresponding to FIG. 4)
"low-high-high-low": the structure with open pore films stacked in the order: absorbent body, low open pore ratio face, high open pore ratio face, high open pore ratio face, low open pore ratio face, front sheet (corresponding to FIG. 5)
"low-high-low-high": the structure with open pore films stacked in the order: absorbent body, low open pore ratio face, high open pore ratio face, low open pore ratio face, high open pore ratio face, front sheet (corresponding to FIG. 6)
NSAM: no seepage to front sheet and adequate masking effect achieved
NS: no seepage to front sheet
S: seepage to front sheet In the Table, 3.3 g/cm² is the value obtained by dividing the weighting of the terminal of the thickness gauge by the terminal area. Furthermore, 20 g/cm² is the value obtained by putting a weight on the top part of the thickness gauge terminal, arranging so that pressure is applied from the 20 g/cm² weighting, and performing measurement.

From Table 1, it may be understood that for cases of 20 g/cm² weighting, with a thickness of 0.4 mm or greater, there is no seepage, giving a good concealing effect. In addition, it may be understood that also in cases where urethane foam is used for the masking members, a masking effect similar to that with porous film is realized.

Examination of Porous Film Stacked Pattern

As described above, the masking effects of the masking members differ as the porous film stacked pattern differs. Therefore, an examination was performed of stacked patterns producing optimal masking effects. Testing was carried out using the same method as in the above described seepage tests. The results are shown in Table 2.

TABLE 2

| Material | Number of layers | Stacked pattern | In mm under pressure 3.3 g/cm² | In mm under pressure 20 g/cm² | Seepage test results |
|---|---|---|---|---|---|
| Porous film B | 2 | high-low-high-low | 0.89 | 0.73 | S |
| Porous film B | 2 | low-high-low-high | 0.89 | 0.73 | NSAM |

Explanation of Terms
"high-low-high-low": porous films stacked in the order: absorbent body, high open pore ratio face, low open pore ratio face, high open pore ratio face, low open pore ratio face, front sheet (corresponding to FIG. 7)
"low-high-low-high": porous films stacked in the order: absorbent body, low open pore ratio face, high open pore ratio face, low open pore ratio face, high open pore ratio face, front sheet (corresponding to FIG. 6)

From Table 2, in cases where porous films are stacked in a high-low-high-low pattern (corresponding to FIG. 7), body fluid from the pores of the porous film, that spreads out in the direction of the absorbent body by the body pressure acting, causes "wet back" (in the direction of the arrows in FIG. 7.) In these cases, the body fluid follows the pores 54 in FIG. 7, and migrates as is, to the front sheet.

On the other hand, in cases where the porous films are stacked in a low-high-low-high pattern (corresponding to FIG. 6), when body pressure acts, the body fluid flows into the recesses 55, but the upper face thereof is blocked. As a result, contact between the front sheet and the absorbent body can be effectively shut off, and seepage of the body fluid to the front sheet can be prevented.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. An absorbent article comprising:
   a front sheet;
   a rear sheet;
   an absorbent body disposed between the front and rear sheets, the absorbent article having, when worn, a longitudinal direction lying in the front-back direction of a wearer, and a short direction lying in the left-right direction of the wearer; and
   a pair of masking members disposed between the front sheet and the absorbent body in the vicinity of the two ends of the short direction of the absorbent body, along the longitudinal direction,
   wherein no masking member is present in the vicinity of longitudinal ends of the absorbent body
   wherein each of the pair of masking members comprises a stack comprising an upper porous film and a lower porous film, the upper porous film having a plurality of pores and being placed on a side of the absorbent article that is closer to the wearer when worn and the lower porous film having a plurality of pores and being placed on a side of the absorbent article opposite the side of the absorbent article that is closer to the wearer when worn,
   wherein circumferential ribs are formed on each of the upper and lower porous films that extend from edges of the plurality of pores on one face of each of the upper and lower porous films to another face of each of the upper and lower porous films,
   wherein the circumferential ribs each have a tapered shape with a diameter that decreases toward an extremity of each rib, and
   wherein the upper porous film is arranged to put extremities of the upper porous film on a side of the masking member closer to the wearer when worn and the lower porous film is arranged to put extremities of the lower porous film on a side of the masking member closer to the absorbent body.

2. The absorbent article according to claim 1, wherein the thickness of each of the pair of masking members is 0.4 mm or greater under a load of 20 g/cm².

3. The absorbent article according to claim 1, wherein the circumferential ribs are configured to act as a valve in the upper porous film and lower porous film to adjust a flow of a fluid when it moves back to the front sheet from the absorbent body.

4. The absorbent article according to claim 1, wherein the upper porous film and lower porous film each comprise foam having continuous cells.

5. The absorbent article according to claim 1, wherein the masking members are disposed above the front sheet.

6. The absorbent article according to claim 1, wherein the masking members, the front sheet, the rear sheet, and the absorbent body are integrally joined in the vicinity of the two ends of the short direction of the absorbent body.

7. The absorbent article according to claim 1, wherein the masking members are pigmented.

8. The absorbent article according to claim 1, wherein the masking members are configured so that a tensile force acting in the longitudinal direction causes the absorbent to flex in the front side and fit the shape of the wearer.

9. The absorbent article according to claim 1, wherein the upper porous film and the lower porous film each comprise continuous cells.

10. The absorbent article of claim 1, wherein the masking members are disposed in the vicinity of the two ends of the short direction of the absorbent body thereby enabling an accumulation of body fluids at one or more of the two ends of the longitudinal direction to be visually determined as an indication of a state in which the absorbent article with accumulated body fluids should be replaced.

* * * * *